United States Patent
Braunberger

(10) Patent No.: US 8,077,553 B2
(45) Date of Patent: Dec. 13, 2011

(54) TIMING SYSTEM AND DEVICE AND METHOD FOR MAKING THE SAME

(75) Inventor: Alfred S. Braunberger, Sequim, WA (US)

(73) Assignee: Vision Works IP Corporation, Sequim, WA (US)

(*) Notice: Subject to any disclaimer, the term of this patent is extended or adjusted under 35 U.S.C. 154(b) by 0 days.

(21) Appl. No.: 12/499,634

(22) Filed: Jul. 8, 2009

(65) Prior Publication Data

US 2009/0266291 A1 Oct. 29, 2009

Related U.S. Application Data

(63) Continuation of application No. 11/902,728, filed on Sep. 21, 2007, now Pat. No. 7,813,226, which is a continuation-in-part of application No. 10/865,724, filed on Jun. 9, 2004, now Pat. No. 7,372,780, which is a continuation-in-part of application No. 10/376,672, filed on Feb. 26, 2003, now Pat. No. 6,822,931, which is a continuation-in-part of application No. 10/319,233, filed on Dec. 13, 2003, now Pat. No. 6,801,477.

(51) Int. Cl.
*G04F 1/00* (2006.01)
*G04F 8/00* (2006.01)
*G01D 21/00* (2006.01)

(52) U.S. Cl. .......................... 368/114; 368/327; 116/206

(58) Field of Classification Search .................. 368/10, 368/113, 114, 121, 327; 116/206, 216; 324/432, 324/435; 374/100–106; 429/90, 93
See application file for complete search history.

(56) References Cited

U.S. PATENT DOCUMENTS

| 3,613,002 | A |   | 10/1971 | Trenkler et al. |         |
|-----------|---|---|---------|-----------------|---------|
| 3,638,120 | A |   | 1/1972  | Jost            |         |
| 3,942,467 | A |   | 3/1976  | Witonsky        |         |
| 3,999,946 | A |   | 12/1976 | Patel et al.    |         |
| 4,153,345 | A | * | 5/1979  | Duchene et al.  | 359/297 |
| 4,212,153 | A |   | 7/1980  | Kydonieus et al.|         |
| 4,277,974 | A | * | 7/1981  | Karr et al.     | 374/102 |
| 4,308,486 | A |   | 12/1981 | Gange           |         |
| 4,327,117 | A |   | 4/1982  | Lenack et al.   |         |
| 4,392,236 | A |   | 7/1983  | Sandstrom et al.|         |
| 4,488,780 | A |   | 12/1984 | Nicholson       |         |
| 4,629,330 | A |   | 12/1986 | Nichols         |         |
| 4,804,275 | A | * | 2/1989  | Kang et al.     | 374/162 |
| 4,860,269 | A | * | 8/1989  | Hennings et al. | 368/107 |

(Continued)

FOREIGN PATENT DOCUMENTS

WO 01/82006 A1 1/2001

(Continued)

*Primary Examiner* — Vit Miska
(74) *Attorney, Agent, or Firm* — Haverstock & Owens

(57) ABSTRACT

A timing device for indicating a passage of a duration of time is disclosed. The timing device in accordance with the embodiments of the invention has a grid array architecture. The grid array architecture includes an electrode structure with an anode layer, a cathode layer and a thermistor layer. The anode layer and the thermistor layer are electrically coupled through a plurality of cathode line structures. In operation the timing device is actuated through a suitable mechanism to initiate depletion of the anode layer and, thereby, indicate a passage of a duration time. As the anode layer depletes, sequential cathode line structures are exposed and the thermistor layer acts as a variable resistor through a plurality of exposed cathode line structures.

9 Claims, 11 Drawing Sheets

U.S. PATENT DOCUMENTS

| | | | |
|---|---|---|---|
| 4,929,090 A * | 5/1990 | Grahm | 374/102 |
| 5,034,233 A | 7/1991 | McCoy, Jr. | |
| 5,045,283 A | 9/1991 | Patel | |
| 5,053,339 A | 10/1991 | Patel | |
| 5,085,802 A | 2/1992 | Jalinski | |
| 5,182,212 A | 1/1993 | Jalinski | |
| 5,254,473 A | 10/1993 | Patel | |
| 5,339,024 A * | 8/1994 | Kuo et al. | 324/435 |
| 5,368,905 A | 11/1994 | Ohno | |
| 5,418,086 A * | 5/1995 | Bailey | 429/93 |
| 5,420,000 A | 5/1995 | Patel et al. | |
| 5,446,705 A | 8/1995 | Haas | |
| 5,544,925 A | 8/1996 | Ikeda | |
| 5,602,804 A | 2/1997 | Haas | |
| 5,633,835 A | 5/1997 | Haas et al. | |
| 5,667,303 A | 9/1997 | Arens et al. | |
| 5,672,465 A | 9/1997 | Patel et al. | |
| 5,699,326 A | 12/1997 | Haas et al. | |
| 5,709,472 A | 1/1998 | Prusik et al. | |
| 5,756,356 A | 5/1998 | Yanagi et al. | |
| 5,785,354 A | 7/1998 | Haas | |
| 5,797,344 A | 8/1998 | Ramsey et al. | |
| 5,802,015 A | 9/1998 | Rothschild et al. | |
| 5,822,280 A | 10/1998 | Haas | |
| 5,830,683 A | 11/1998 | Hendricks et al. | |
| 5,912,759 A * | 6/1999 | Good et al. | 359/297 |
| 5,930,023 A * | 7/1999 | Mitchell et al. | 359/270 |
| 5,930,206 A | 7/1999 | Haas et al. | |
| 5,947,369 A * | 9/1999 | Frommer et al. | 235/382 |
| 5,989,852 A | 11/1999 | Hendricks et al. | |
| 5,997,927 A | 12/1999 | Gics | |
| 6,042,264 A | 3/2000 | Prusik et al. | |
| 6,103,351 A | 8/2000 | Ram et al. | |
| 6,113,857 A | 9/2000 | Manico et al. | |
| 6,198,701 B1 * | 3/2001 | De Jonghe et al. | 368/327 |
| 6,244,208 B1 | 6/2001 | Qiu et al. | |
| 6,269,764 B1 | 8/2001 | Adamy et al. | |
| 6,285,492 B1 * | 9/2001 | Good et al. | 359/297 |
| 6,295,252 B1 | 9/2001 | Holt et al. | |
| 6,331,076 B1 | 12/2001 | Coll | |
| 6,373,786 B1 | 4/2002 | Kagan et al. | |
| 6,435,128 B2 | 8/2002 | Qiu et al. | |
| 6,452,873 B1 | 9/2002 | Holt et al. | |
| 6,544,925 B1 | 4/2003 | Prusik et al. | |
| 6,801,477 B2 * | 10/2004 | Braunberger | 368/327 |
| 6,822,931 B2 * | 11/2004 | Braunberger | 368/327 |
| 7,254,095 B1 | 8/2007 | Brunberger | |
| 7,294,379 B2 | 11/2007 | Ko et al. | |
| 7,372,780 B1 | 5/2008 | Braunberger | |
| 7,463,558 B2 | 12/2008 | Brunberger | |
| 2003/0112711 A1 | 6/2003 | Braunberger | |
| 2003/0151985 A1 | 8/2003 | Braunberger | |
| 2007/0268785 A1 | 11/2007 | Braunberger | |
| 2009/0016176 A1 | 1/2009 | Braunberger | |
| 2009/0266291 A1 | 10/2009 | Braunberger | |
| 2010/0149929 A1 | 6/2010 | Braunberger | |

FOREIGN PATENT DOCUMENTS

| | | |
|---|---|---|
| WO | 01/82006 A2 | 11/2001 |
| WO | 03/052524 | 6/2003 |
| WO | 2004/077172 A2 | 10/2004 |
| WO | 2009/038806 A1 | 3/2009 |
| WO | 2010/099340 A2 | 9/2010 |

* cited by examiner

TIMING SYSTEM AND DEVICE AND METHOD FOR MAKING THE SAME

RELATED APPLICATION(S)

This Patent Application is a continuation of the co-pending U.S. patent application Ser. No. 11/902,728, filed on Sep. 21, 2007 and entitled "TIMING SYSTEM AND DEVICE AND METHOD FOR MAKING THE SAME" which is a continuation-in-part of the U.S. patent application Ser. No. 10/865,724 filed Jun. 9, 2004 and entitled "TIMING SYSTEM AND DEVICE AND METHOD FOR MAKING THE SAME," now U.S. Pat. No. 7,372,780 B1, which is a continuation-in-part of the U.S. patent application Ser. No. 10/376,672, filed Feb. 26, 2003 and entitled "TIMING SYSTEM AND DEVICE AND METHOD FOR MAKING THE SAME," now U.S. Pat. No. 6,822,931 B2, which is a continuation-in-part of the U.S. patent application Ser. No. 10/319,233 filed Dec. 13, 2002, and entitled "TIMING SYSTEM AND DEVICE AND METHOD FOR MAKING THE SAME," now U.S. Pat. No. 6,801,477 B2.

The co-pending U.S. patent application Ser. No. 11/902,728, filed on Sep. 21, 2007, and entitled "TIMING SYSTEM AND DEVICE AND METHOD FOR MAKING THE SAME," and the U.S. Pat. Nos. 7,372,780 B1, 6,822,931 B2 and 6,801,477 B2 are all hereby incorporated by reference.

FIELD OF THE INVENTION

The invention relates to timing systems and devices and a method for making the same. More specifically, the invention relates to systems and devices for and methods of indicating the passage of a duration time.

BACKGROUND OF THE INVENTION

There are a number of different timing systems and devices, generally referred to as time-temperature indicators (TTIs), which can be used to monitor the exposure of objects to a range of temperatures over a specified period of time. In an early example, Witonsky, in U.S. Pat. No. 3,942,467, describes a time-temperature indicator with an encapsulated inner container and a pH sensitive dye solution contained therein. The device of Witonsky further has an encapsulated outer container containing an organic material which undergoes solvolysis. The outer container and the inner container are separated by a membrane. When the membrane between the inner container and the outer container is broken, the contents of the containers mix and over a period of time change color, thus providing an indication of the passage of a duration of time. A number of other time-temperature indicators utilize wicking techniques (such as described in U.S. Pat. Nos. 5,709,472 and 6,042,264, both issued to Prusik et al.) or diffusion layer techniques (such as described in U.S. Pat. No. 4,629,330 issued to Nichols and U.S. Pat. Nos. 5,930,206 and 5,633,835 both issued to Haas et al.). In U.S. Pat. No. 6,198,701 issued to De Jonghe et al., an electrochemical timing device is described, whereby consumption of an electrode is used to provide an indication of the passage of a duration of time.

Time-temperature indicators can have a number of different applications for indicating when an event or activity needs to take place. For example, time-temperature indicators have applications for indicating when the perishable materials have expired and need to be thrown out. Time-temperature indicators also have applications for general inventory management, for monitoring projects, activities and a host of other time and/or temperature dependent events. Therefore, there is a continued need to develop reliable timing systems and devices which can be used for a variety of different applications.

SUMMARY OF THE INVENTION

The present invention is directed to a device and system for indicating the passage of a duration of time and a method of making the same. While, the present invention is referred to herein as a timing device, it is understood that the timing device of the present invention can also be sensitive to temperature. While a timing device, in accordance with the embodiments of the invention, can be configured to be more or less sensitive to temperature, the timing device will generally react, or change, at a faster rate at higher temperatures unless the timing device is configured with a temperature compensating element, such as described in detail below.

A timing device, in accordance with the embodiments of the present invention is a chemical-based timing device, electrochemical-based timing device, or a combination thereof. The timing device, when actuated, provides a visual indication of a passage of time. The timing device is configured as a "stand alone" indicator or, alternatively, is configured to be coupled with any number of circuits which also provide an audible signal or otherwise sense and/or store information regarding the operation of the device.

In some embodiments, the device comprises a lens, a base and means for altering the visibility of the base through the lens and thereby indicating the passage of a duration of time. In some embodiments, the means for altering the visibility of the base through the lens comprises an optical medium positioned between the lens and the base. The optical medium comprises chemicals and/or elements of a battery that react or otherwise change over time and, thereby alters the visibility of the base through the lens. For example, one or more of the materials, layers or components of the optical medium are converted from opaque to transparent or, alternatively, from transparent to opaque, thereby increasing or decreasing the visibility of the base through the lens, respectfully. Alternately, one or more of the materials, layers or components of the optical medium are dissolved or depleted, thereby altering the visibility of the base through the lens.

In accordance with the embodiments of the invention, the optical medium comprises a solid layer positioned between the lens and the base, also referred to herein as a lens coating layer, and a fluid layer positioned between the solid layer and the base. The fluid layer contains gel, water and any suitable chemical(s) required to change the solid layer from opaque to transparent, change the layer from transparent to opaque, deplete the solid layer or dissolve the solid layer, as explained in detail below. In some embodiments of the invention, the solid layer is opaque and when the device is actuated, the fluid layer dissolves the solid layer over a duration of time, thereby making the base visible through the lens and indicating the passage of a duration of time.

In further embodiments of the invention, a timing device comprises an indicator between the lens and the lens coating layer to enhance the visual indication of the passage of time. Suitable indicators are fluids or solid, and can include, but are not limited to pH indicators and reactive dye indicators, which generate a color change when reacted with the fluid layer, after the fluid layer sufficiently depletes or dissolves the lens coating layer. Alternatively, the lens coating layer is a semi-porous membrane layer, wherein the indicator provides a color change when a sufficient amount of the reactive species from the fluid medium migrates through the membrane layer.

In still further embodiments of the invention, a timing device comprises a battery, wherein at least a portion of the optical medium between the solid layer and the base actively participates in an electrochemical process resulting in a visual change indicating the passage of a duration of time. In accordance with this embodiment of the invention, the battery is a galvanic cell and the optical medium comprises an electrolyte. A galvanic cell is a battery where reduction and oxidation of species within the battery will occur spontaneously as long as there is a conductive path from a first electrode of the cell to a second electrode of the cell. In operation a material within the electrolyte is plated between the base and the lens, thereby reducing the visibility of the base through the lens. Alternatively, an opaque electrode positioned between the lens and the base is depleted, thereby increasing the visibility of the base through the lens.

In still further embodiments of the invention, the battery is an electrolytic cell. An electrolytic cell requires a current from another battery, or other current source, to drive the reduction and oxidation of species within the battery. In accordance with this embodiment, a current from an external battery, or current source, flows through the battery and a material within the electrolyte is plated out between the lens and the base, thereby reducing the visibility of the base through the lens. Alternatively, an opaque electrode positioned between the lens and the base is depleted, thereby increasing the visibility of the base through the lens.

Regardless of whether a timing device is configured to operate as a galvanic cell or as an electrolytic cell, the timing device can comprise a colored electrolyte. In accordance with the embodiments of the invention, the colored electrolyte becomes visible after depleting one or more electrode materials positioned between a transparent lens and the colored electrolyte, thereby indicating the passage of a duration of time. For example, a timing device comprises a clear lens formed from a polymer, such as polyester. The polyester lens is coated with a first electrode material, such as aluminum. The timing device further comprises a base structure with a second electrode material. The second electrode material is able be any metal with a reduction potential that is different from a reduction potential of the first electrode material. If the device is being operated as an electrolytic cell, as explained above, then the reduction potential of the first electrode material and the second electrode material is able to be the same. Between the first electrode material and the base structure is the colored electrolyte and when the device is activated, the first electrode material is depleted from the transparent lens and the colored electrolyte becomes visible, thereby indicating the passage of the duration of time.

In accordance with further embodiments of the invention, a timing device is configured with a lens structure and/or the base structure formed from a conductive polymer with an electrode material coated thereon. The conductive polymer is believed to help ensure uniform plating and/or depletion of electrode materials when the device is activated, such as described in detail above. Alternatively, or in addition to the use of a conductive polymer, as described above, a metal screen is able to be in contact with, or imbedded in, one or more of the electrode materials to help ensure uniform plating and/or depletion of electrode materials.

In still further embodiments of the invention, a timing device is configured to operate as an electrochemical cell and includes an electrolyte with an indicator. For example, the timing device comprises an electrolyte with a pH indicator that changes color when the electrochemical cell is activated, such as described above, and the electrochemical cell generates a sufficient concentration of an ion or a pH altering species within the electrolyte.

A timing device, in accordance with the embodiments of the invention, is actuated using any number of different mechanisms or combination of mechanisms. For example, where the timing device is a chemical-based timing device, the timing device is formed in parts, wherein a first part comprises a first reactive region and a second part comprises a second reactive region. To form an activated device, the first part and the second part are brought together and the first reactive region and the second reactive region are held eclipsed and in contact. Alternatively, a chemical-based timing device comprises a membrane or a removable structure separating the reactive regions of the device, wherein the membrane is broken or the structure is removed to activate the device.

In some embodiments, where the timing device is an electrochemical-based timing device, the device is actuated by a switch mechanism that closes a circuit between electrode elements of a galvanic or an electrolytic cell. Alternatively, the device is fabricated in parts as described above, wherein the parts have contact features, which when brought together close a circuit between the electrode elements of a galvanic or an electrolytic cell. An actuator switch, in accordance with further embodiments of the invention, is in electrical communication with a thermosensor, wherein the thermosensor instructs the actuator switch to close a circuit between electrode elements of a galvanic or an electrolytic cell within a range of temperatures.

In accordance with yet further embodiments of the invention, a timing device and system comprises a photo-sensitive component, element or film. For example, a timing device comprises a piece of photographic film, which is color film, black and white film or a combination thereof. The photographic film is formed from a base with a photographic medium coated or deposited thereon, wherein the photographic film is capable of being activated to change color or shade and thereby indicate the passage of a duration of time. The photographic material is any photographic medium, but in some embodiments comprises a silver-based material including, but not limited to, silver chloride, silver fluoride, silver iodide and/or combinations thereof. In yet other embodiments of the invention the photographic medium comprises a silver-soap ($Ag^+$ cations in a fatty acid such as stearic acid) often used in thermally-activated films. Where the photographic medium is a silver halide, the silver halide is mixed with a binder, such as cellulose or gelatin, to hold the silver halide material on the base.

The photographic material, in accordance with the embodiments of the invention, is made to be thermally and/or light sensitive using any number of techniques known in the art, including the addition of sulfur and gold and/or a dye, such as an infrared absorbing dye. To activate the photographic medium a developer is applied to the film. There are a number of materials that is able to be used for developing photographic materials, such as hydroquinone-based developers. Generally, all developers contain chemicals that assist in the reduction of silver halide or silver cations to form a darkened or colored image.

In accordance with the embodiments of the invention, a developer is incorporated into the construction of the film and a timing device is thermally activated or is activated by removing a barrier between the photographic material and the developer. Alternatively, the photographic material and the developer are included on separate parts or regions of a timing device and are activated by bringing together a part or region of the film with the photographic material with a part or region of the film with the developer.

In accordance with yet further embodiments of the invention, a device comprises a film with zones that change color at different rates and, therefore, provide an indication of the passage of a range of times. Each of the zones comprises a photographic material, as explained above, or other chemical and/or electro-chemical materials that can be activated to change color at different rates. When the zones comprise photographic materials, the zones are made to have different reaction rates by using photographic materials with different sensitivities to heat, light and/or developer, and/or by varying the thickness of diffusion layers deposited over the zones. In accordance with further embodiments of the invention, the zones are made to have different rates of reaction and/or sensitivity to a developer by pre-treating the zones to a range of different light and/or heat exposures, wherein the zones with longer exposures will develop and change color faster than zones with shorter exposures.

A system, in accordance with the embodiments of the invention, comprises a timing film, such as described above, and further comprises an adhesion layer for attaching pieces of film to consumer articles, such as containers of leftover food. In some embodiments, the system also comprises a dispenser for conveniently dispensing pieces of film from a stack or roll of the timing film and means, such as a magnet, for attaching the dispenser to a household appliance.

In accordance with the embodiments of the invention, a timing device comprises an electrochemical structure, such as described above, that is capable of being activated and configured to generate an audio and/or visual response to indicate passage of a duration of time after being activated. In some embodiments, the timing device also comprises a compensating element such as a varistor, a thermistor and/or combinations thereof. The compensating element is electrically coupled to the electrochemical structure and regulates the time for the response with respect to changes in temperature.

In still further embodiments of the invention, a timing device comprises an electrochromic structure configured to generate a visual indication in a prescribed period of time after being activated. In some embodiments, the timing device also comprises a driver circuit. The driver circuit is electrically coupled to the electrochromic structure and is configured to actuate electrochromic structure in the prescribed period of time. The driver circuit is able to include a timing circuit and a battery structure. Further, the timing circuit is able to be programmable to generate a visual indication in a range of prescribed periods of time. Also, the timing device is able to include zones which are each configured to indicate a passage of a different and predetermined duration of time.

In accordance with yet further embodiments of the invention, a timing device comprises an electrochemical structure and an indicating layer. In some embodiments, the electrochemical structure comprises an indicating electrolyte, a top electrode and a bottom electrode with the indicating layer proximal with the top electrode. In operation, the top and the bottom electrodes are electrically coupled and the top electrode is depleted or partially depleted, allowing the indicating electrolyte to come into contact with the indicating layer and thus generate a visual indication of the passage of time.

In accordance with still further embodiments of the invention, a timing device comprises electrodes that sandwich a solid-state electrolyte. Suitable solid-state electrolytes include, but are not limited to, silver halide (e.g. AgI and $RbAg_4I_5$), silver selenide (e.g. $Ag_2Se$), sodium ion complexes (e.g. sodium β-Aluminum and NASICON), lithium ion complexes (e.g. $LiCoO_2$, $LiNiO_2$ and $LiMnO_2$), oxides (e.g. cubic stabilized $ZrO_2$, δ-$Bi2O_3$, and defect Perovskites) and Fluoride ion complexes (e.g. $PbF_2$, $BaF_2$, $SrF_2$ and $CaF_2$). In accordance with these embodiments, depletion or partial depletion of at least one of the electrodes provides or initiates a visual indication of a passage of a duration of time, such as described in detail above. The timing device can also include a switch mechanism, a compensating element and/or an indicator, such as a pH indicator, also described in detail above. In yet further embodiments, the timing device includes a plurality of sub-cells or zones that collectively provide a visual indication of a passage of a range of durations of time.

In accordance with a method of the invention, a timing device is formed in parts, such as described with reference to FIGS. 3A-C. For example, a first electrode structure is formed on a first piece of a substrate and a second electrode structure is formed on a second piece of a substrate, wherein at least one of the first electrode structure and the second electrode structure comprises a solid-state electrolyte. In operation the first electrode structure and the second electrode structure are configured to contact each other in a sandwich-like configuration to thereby actuate the timing device and provide a visual indication of a passage of a duration of time. The substrates can be formed from any number of different materials or combinations of materials including glass, metal, plastic and combinations thereof. In some embodiments, the substrates are formed from plastic, such as polyester or another similar transparent material. In accordance with yet further embodiments of the invention, a removable protective layer is formed over the first electrode structure and the second electrode structure and is removed prior to placing the first electrode structure and second electrode structure in contact with each other.

In accordance with yet further embodiments of the invention, a timing device has what is referred to herein as a grid array architecture. In accordance with this embodiment, a suitable electrolyte is formed or placed on a suitable base material. Over the electrolyte an anode layer, such as an aluminum layer, and a cathode layer, such as copper layer, are formed. In some embodiments, the cathode layer is not in direct contact with the electrolyte, while the anode layer is in direct contact with the electrolyte. A thermistor layer is formed along side of the anode layer and cathode layer. An array of cathode line structures are formed over the anode layer and the thermistor layer to provide contacts between the anode layer and the thermistor layer. At least one contact line between the cathode layer and the thermistor layer. The anode layer, the cathode layer, the thermistor layer, the cathode line structures and the contact line are formed using any suitable technique known in the art including, but not limited to, vapor deposition, sputtering and micro-printing techniques.

A timing device with a grid array architecture preferably includes a mechanism for activating the timing device, such as described above and below. When the timing device is activated the anode layer begins to deplete in a direction away from the cathode layer, thereby exposing sequentially positioned cathode line structures. The exposed cathode line structures provide points of internal resistance to current flow and thus control the rate that the anode layer is depleted. The number, the spacing, the thicknesses and geometries of the cathode line structures, as well as the anode layer, the cathode layer and thermistor layer, are designed or tailored for the application at hand. Further, the material used to form the thermistor layer, in accordance with the embodiments of the invention, is selected to regulate the overall depletion rate of the anode is independent of temperature.

BRIEF DESCRIPTION OF THE DRAWINGS AND ATTACHMENTS

FIGS. 1A-B show a schematic representation of a timing device, in accordance with the embodiments of the invention.

FIG. 2 shows a schematic representation of a timing device, in accordance with an embodiment of the invention.

FIGS. 3A-C show systems for assembling timing devices, in accordance with the method of the present invention.

FIGS. 4A-C show schematic cross sectional views of several timing device configurations, in accordance with the embodiments of the invention.

Figure 7A:
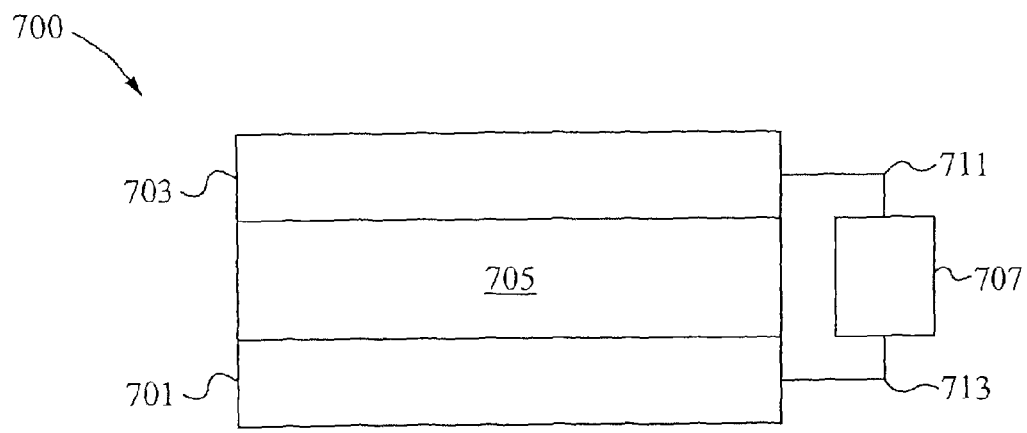
Figure 7B:
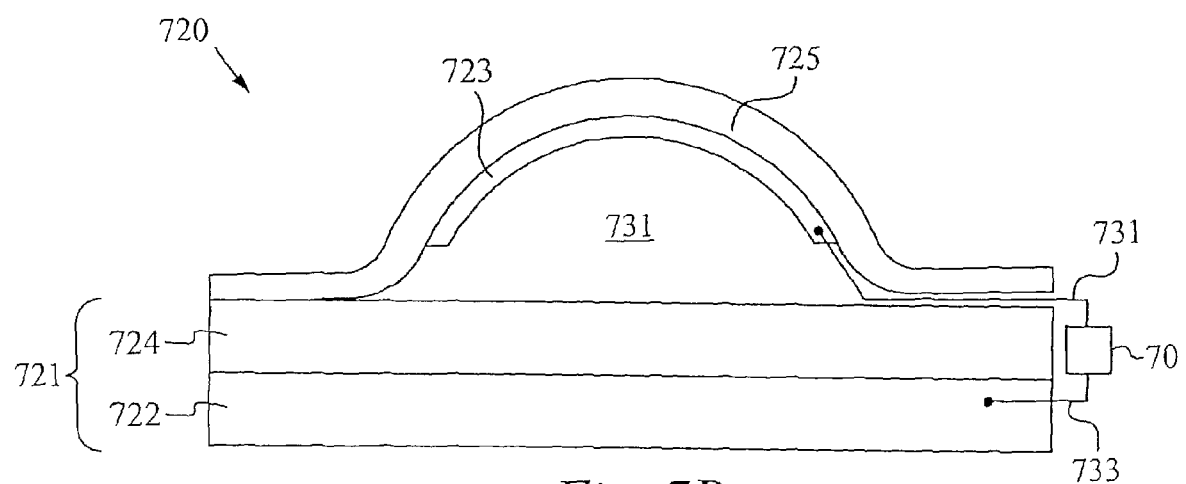

FIGS. 7A-B show schematic cross-sectional views of timing device configurations with compensator elements, in accordance with the embodiments of the invention.

Figure 8A:
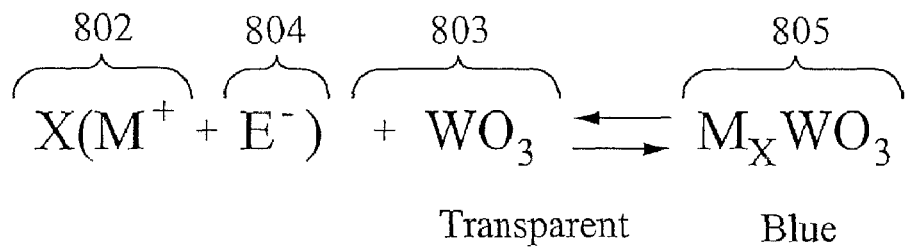

FIG. 8A shows a reversible reaction sequence for an electrochromic material used in a timing device, in accordance with the embodiments of the invention.

Figure 8B:
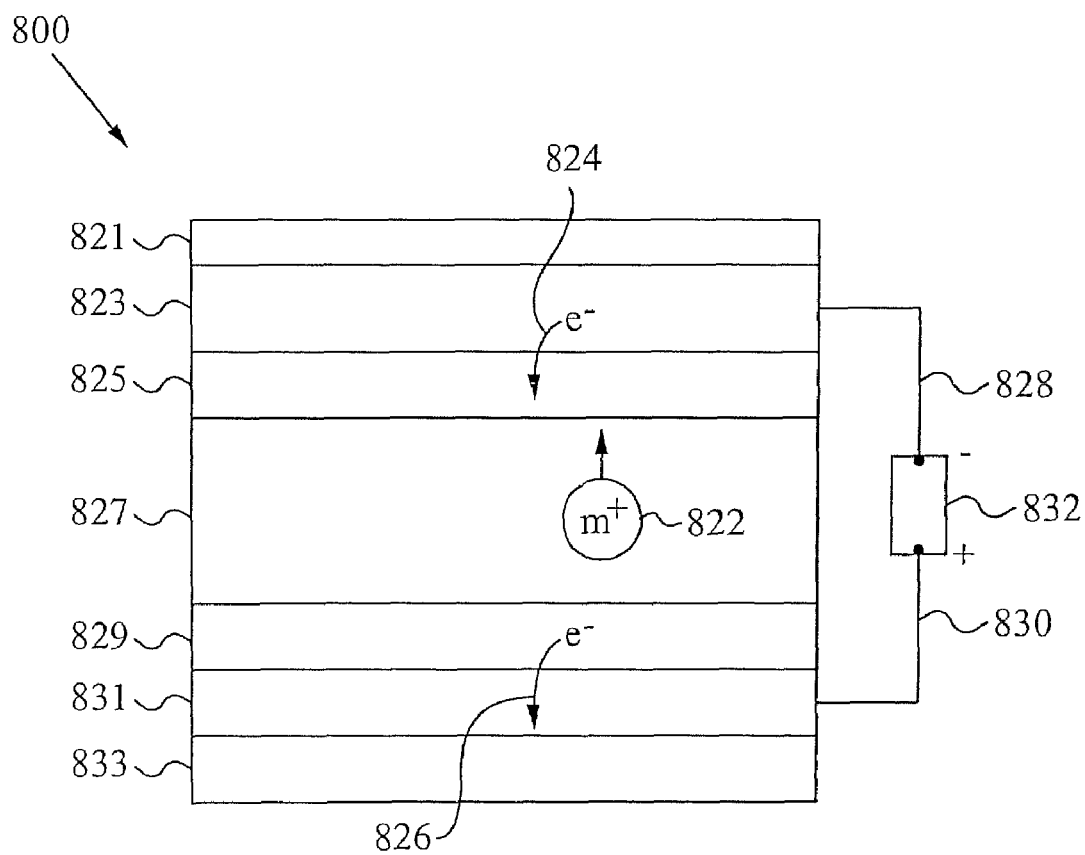

FIG. 8B shows a multi-layer construction for an electrochromic device, in accordance with the embodiments of the invention.

Figure 9A:
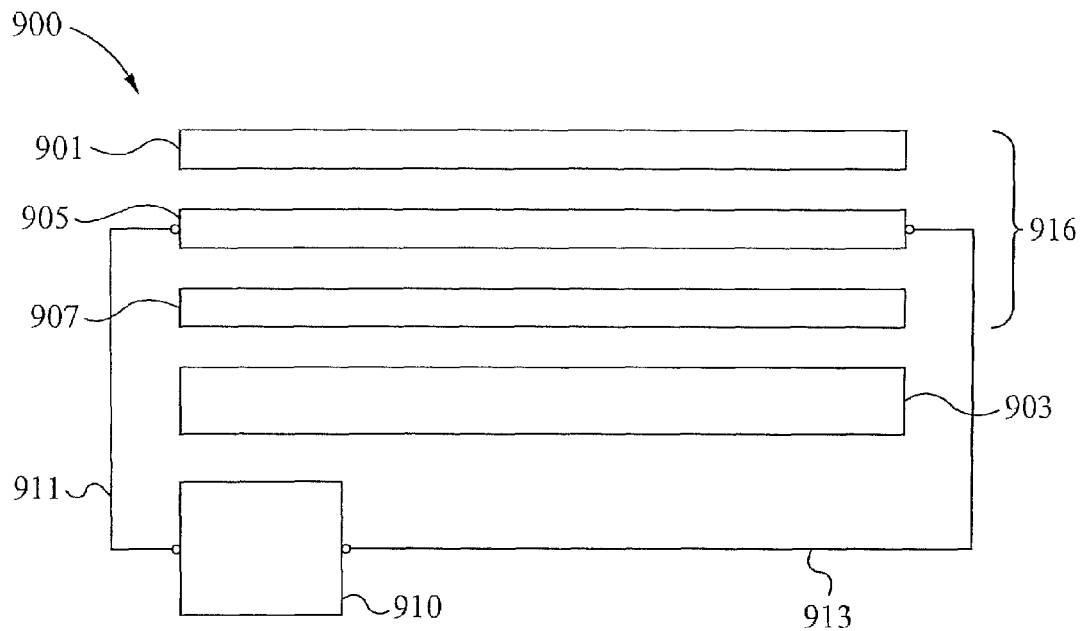
Figure 9B:
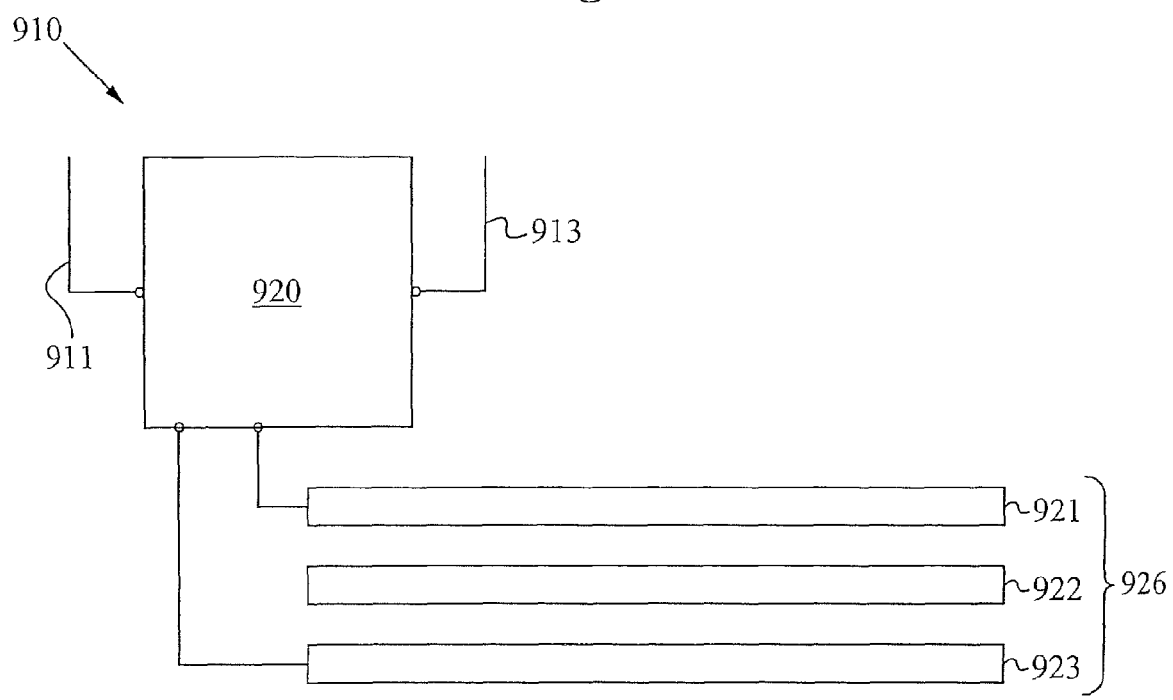

FIGS. 9A-B show a timing device with a timer circuit, in accordance with the embodiments of the invention.

Figure 10:
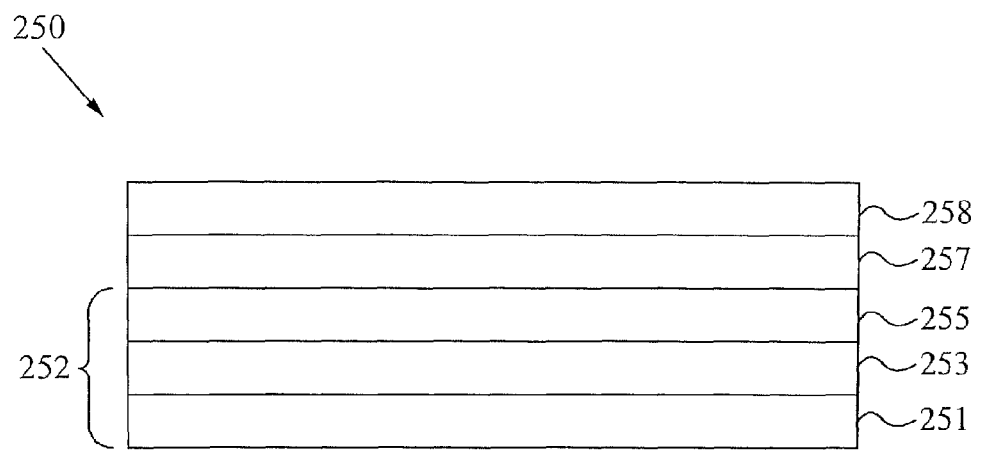

FIG. 10 shows a schematic representation of a timing device comprising an indicating electrolyte and an indicating layer, in accordance with the embodiments of the invention.

Figure 11:
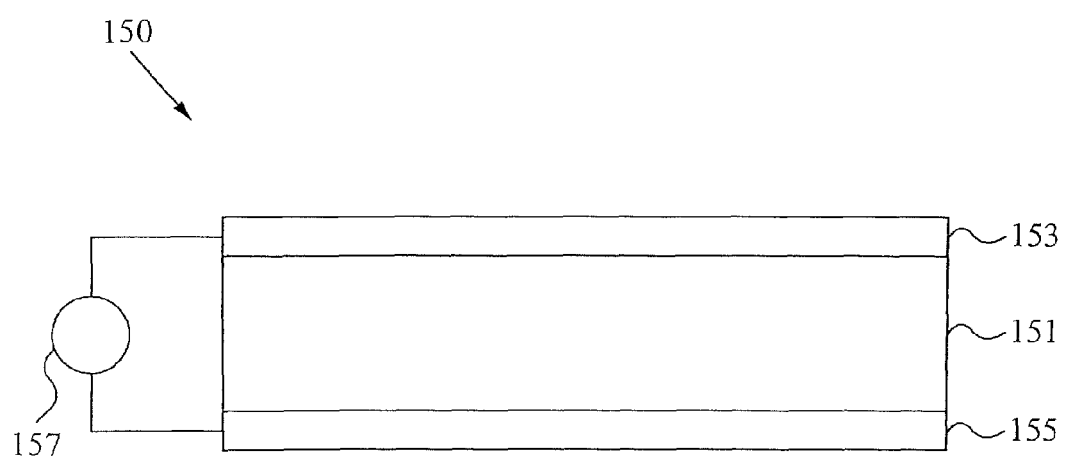

FIG. 11 shows a schematic representation of a timing device comprising a solid-state electrolyte, in accordance with the embodiments of the invention.

Figure 12:
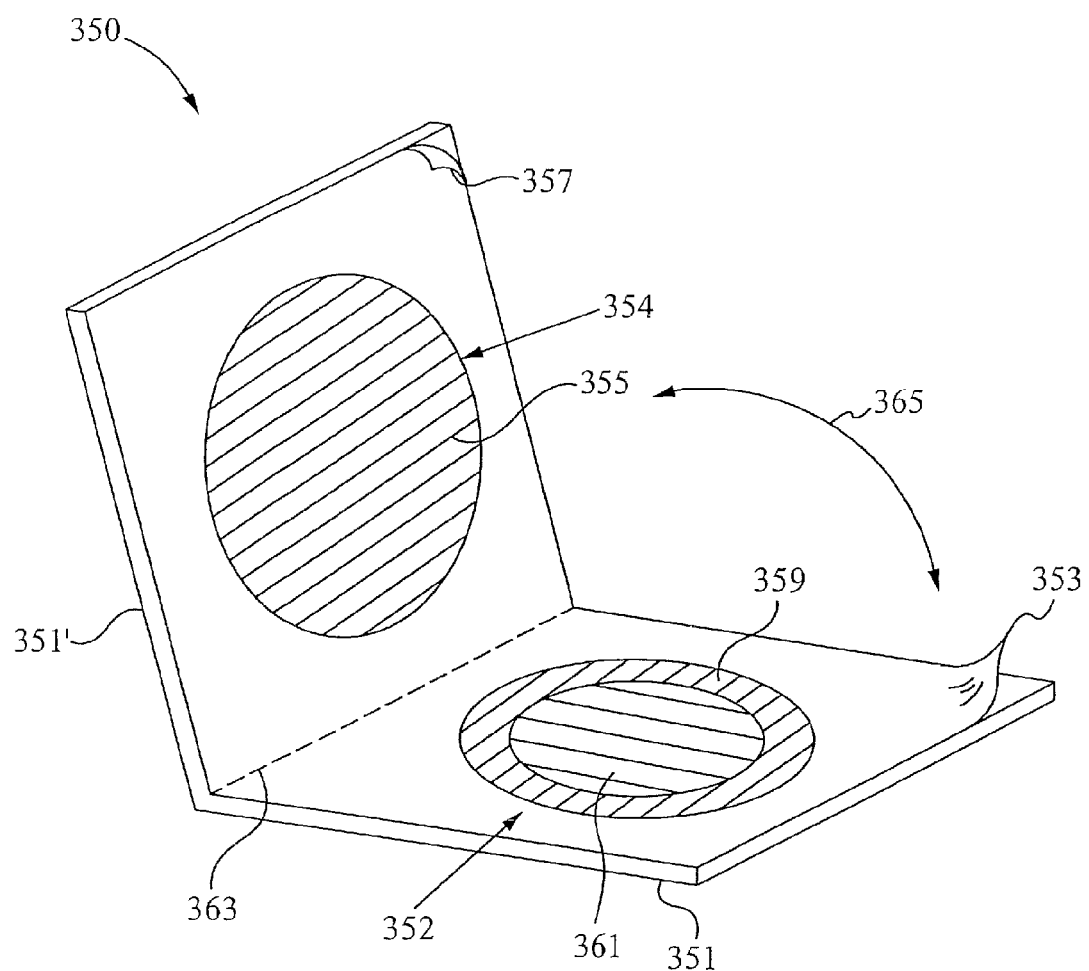

FIG. 12 shows a schematic representation of a timing device comprising a solid-state electrolyte, in accordance with further embodiments of the invention.

Figure 13A:
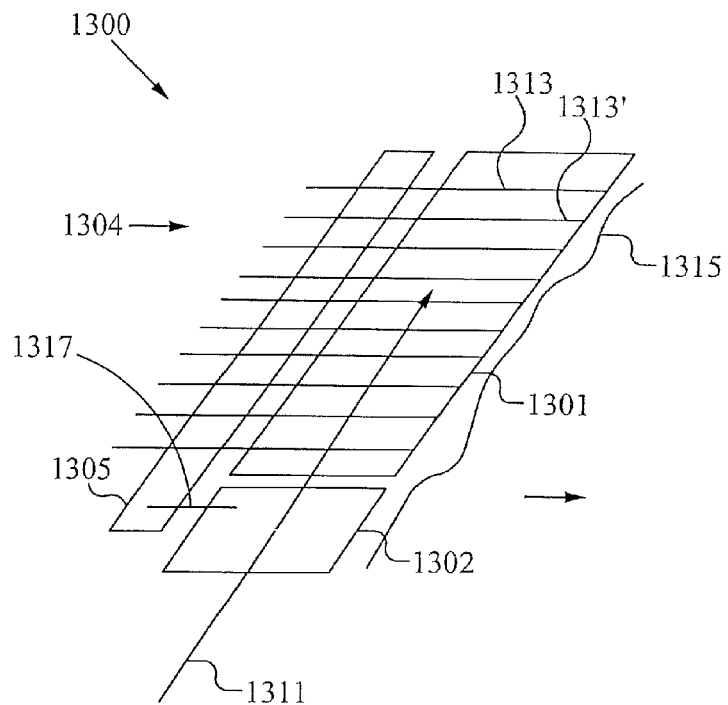
Figure 13B:
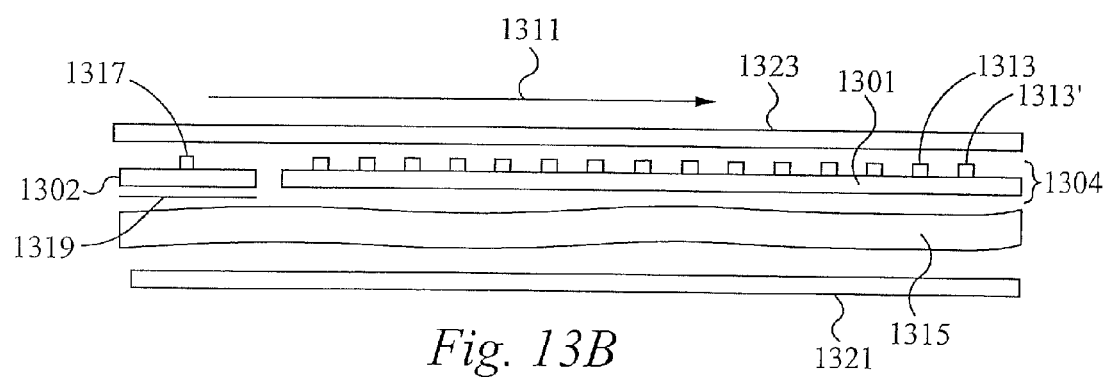

FIG. 13A-B show schematic representations of a timing device with a grid array architecture, in accordance with further embodiments of the invention.

DETAILED DESCRIPTION OF THE INVENTION

Figure 1A:
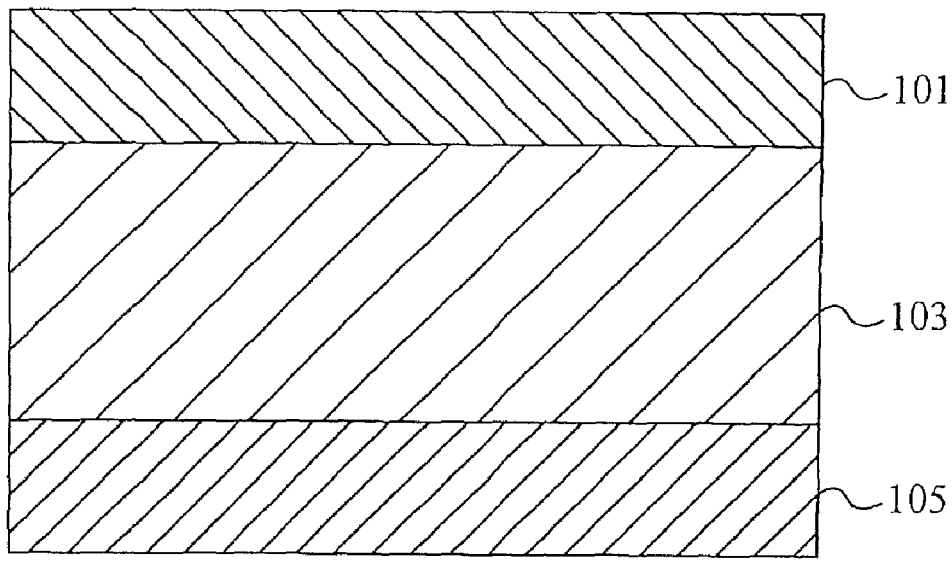
Figure 1B:
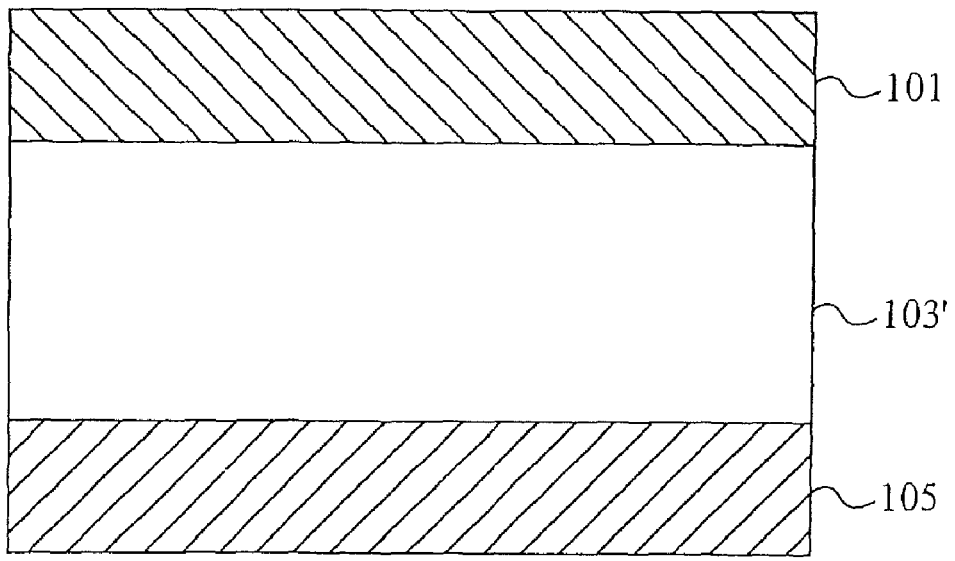

Referring to FIGS. 1A-B, a timing device 100, in accordance with the embodiments of the invention is a chemical-based timing device, an electrochemical-based timing device, or a combination thereof. The timing device 100 comprises a transparent lens 101, a base 105 and an optical medium 103 therebetween. When the device 100 is actuated, the optical medium 103 is changed to a modified medium 103', thereby altering the visibility of the base 105 through the lens 101 indicating the passage of a duration of time. The lens 101 and base 105 are formed from any suitable material, or combination of materials, including, but not limited to polymers and plastic materials.

Still referring to FIGS. 1A-B, the optical medium 103 comprises any number of different chemicals or elements which over the duration of time alter the visibility of the base 105 through the lens, as explained in detail below. In some embodiments, however, the base 105 becomes more visible through the lens 101 when the device 100 has expired. In order to enhance the visibility of the base 105 through the lens 101, when the device 100 has expired, the base 105 is brightly colored and/or has indicia printed thereon, such that the bright color and/or the indicia are visible through the lens 101 when the device is expired.

Figure 2:
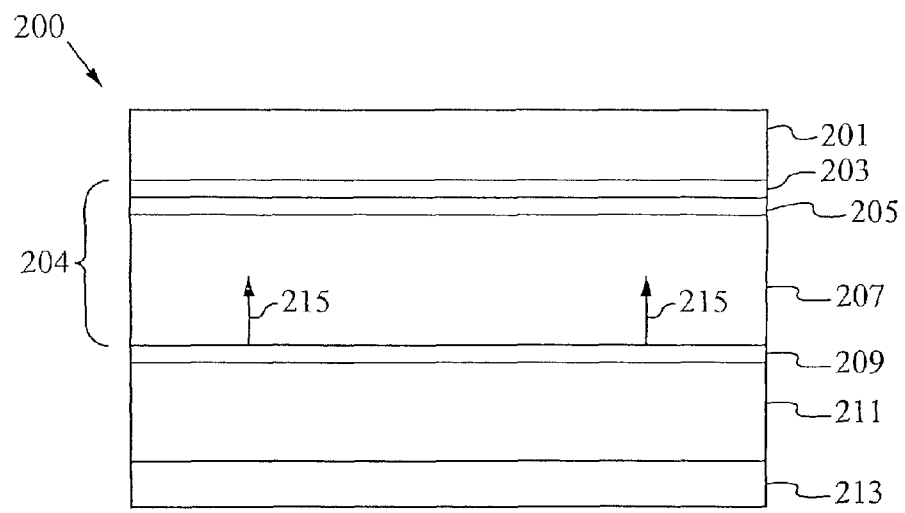

Referring now to FIG. 2, in accordance with some embodiments of the invention, a timing device 200 comprises a lens 201, a base 211 and an optical medium 204, as described above. In some embodiments, the optical medium 204 comprises a fluid layer 207. The fluid layer 207 can be comprised of any number of fluid materials, but in some embodiments comprises a transparent gel material, which is either acid or basic and which is either conductive or insulating, depending on the application at hand. In some embodiments, the optical medium 204 also comprises an opaque layer 205, also referred to herein as a lens coating layer, which does not imply that the opaque layer 205 is necessarily coated directly on the lens 201. The lens coating 205 is formed from a material which will react with the fluid layer 207, when the device 200 is activated. For example, the lens coating layer 205 is formed from a hardened gel, such as gelatin and thiosulfate. In some embodiments, the liquid layer 207 dissolves the lens coating layer 205 when the device 200 is activated, thereby increasing the visibility of the base therebelow and indicating the passage of a duration of time.

Still referring to FIG. 2, in further embodiments of the invention, a timing device 200 comprises an activation layer 203. The activation layer 203 comprises an indicator, such as a pH indicator which reacts with the fluid layer 207, when the fluid layer 207 sufficiently depletes or dissolves the lens coating layer 205. Alternatively, an indicator is incorporated into the lens coating layer 205 and is dissolved or leached by the fluid layer 207, such that when the concentration of the indicator in the fluid layer 207 becomes sufficiently high, the fluid layer 207 changes color.

In still further embodiments of the invention, the lens coating layer comprises a reactive species that reacts with an indicator in the fluid layer 207. For example, the lens coating layer 205 comprises a base material, such as sodium bicarbonate, which is leached from the lens coating layer 205 or is dissolved into the fluid layer 207 from the lens coating layer 205. The fluid layer 207 comprises a pH indicator and an acid material and when a sufficient amount of base material is dissolved into the fluid layer 207, then the acid material is naturalized and the pH indicator changes color, indicating the passage of a duration of time.

In still further embodiments of the invention, a timing device 200 comprises a diffusion material 209. When the device 200 is activated, the diffusion material 209 begins to diffuse through the fluid layer 207, as indicated by the arrows 215. When the diffusion material 209 reaches the lens coating layer 205, the diffusion material 209 reacts with the lens coating layer 205 to provide a color change, dissolve the lens coating layer 205 and react with the indicator layer 203, or any combination thereof, to indicate the passage of a duration of time.

Still referring to FIG. 2, a timing device 200, in accordance with the embodiments of the present invention also comprises an attaching means 213 for attaching the timing device 200 to a product or an object (not shown). The attaching means 213 is any suitable attaching means, and in some embodiments, comprises an adhesive layer for sticking the device 200 onto the product or object.

Figure 3A:
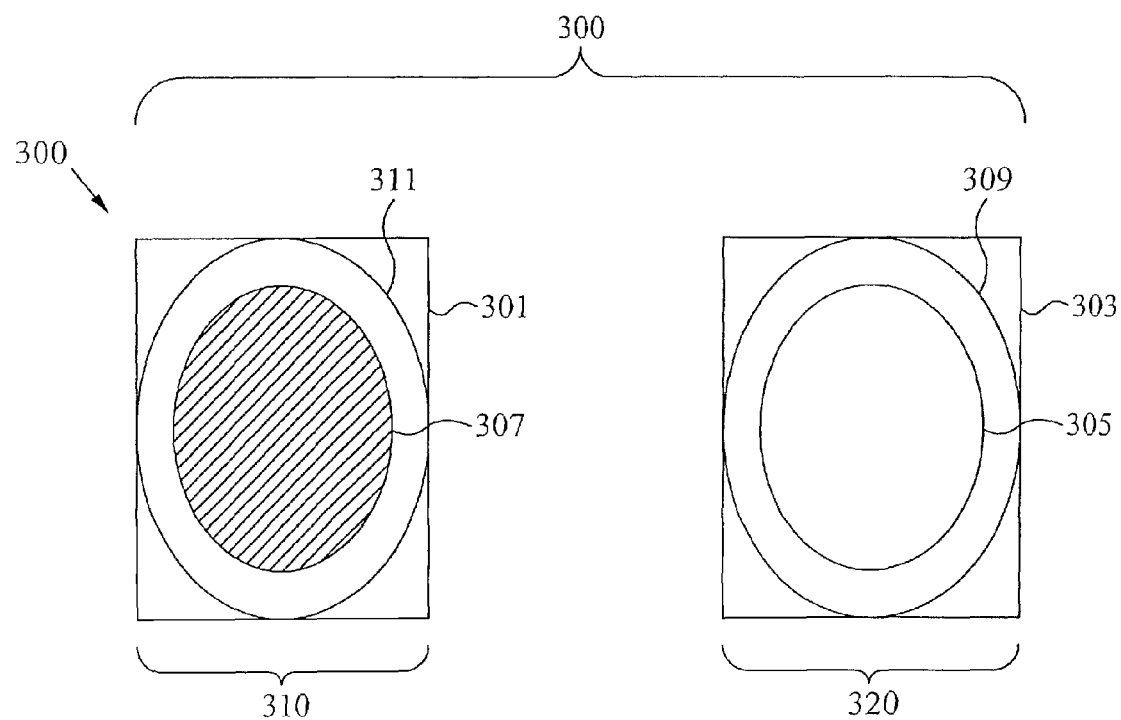

Now referring to FIG. 3A, a timing system 300, in accordance with a method of the invention, is fabricated in parts 310 and 320. A first part 310 of the system 300 comprises a first reactive region 307 formed on a suitable base 301. A second part 320 of the system 300 comprises a second reaction region 305 formed on a clear lens 303. One or both of the parts 310 and 320 comprise adhesive rings 311 and 309. To actuate the system 300, the parts are brought together such that the first reactive region 307 and the second reactive region 305 are eclipsed and in contact with each other. The adhesive rings 311 and 309 hold the first part 310 and the second part 320 together with the reactive regions 305 and 307 eclipsed and in contact. While in contact with each other, the first reactive region 307 and the second reactive region 305, undergo a chemical, physical or electrochemical process which alters the visibility of the base 310 through the lens 303, as described above. Each of the parts 310 and 320 of the system 300, in accordance with further embodiments of the invention, comprise a protective covering (not shown), such as a cellophane, which acts protective of the reactive regions 307 and 305, and is removed prior to use.

Figure 3B:
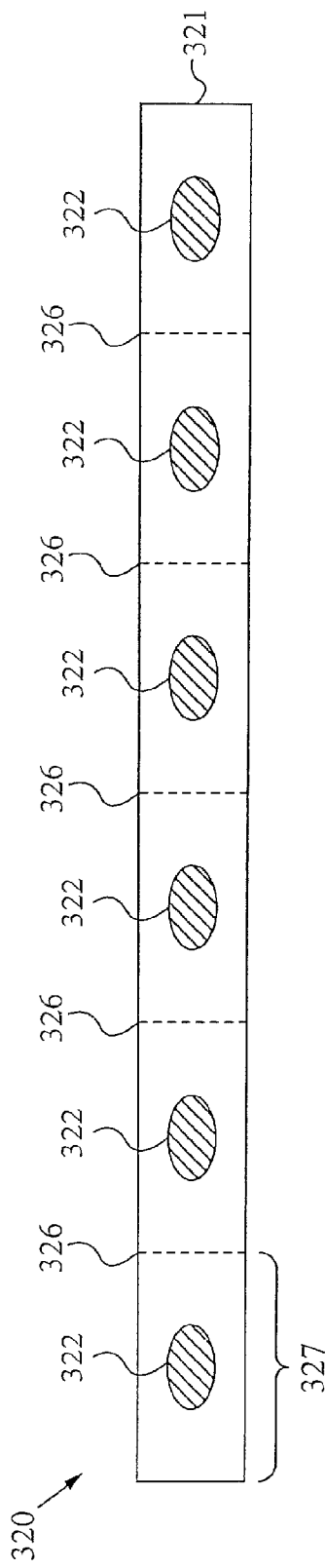

Now referring to FIG. 3B, a system 320, in accordance with the embodiments of the invention, is formed by fabricating a plurality of first reactive regions 322 on a first piece of tape 321 and a plurality of second reactive regions 324 on a second piece of tape 323. In some embodiments, the tapes 321 and 323 have perforations 326 and 328 between each of the first reactive regions 322 and the second reactive regions 324. In some embodiments, the tapes 321 and 323 are configured to be dispensed from a roll dispenser (not shown) or any other suitable dispenser. The dispenser can be dispenser configured to attach to a household appliance using a magnet or any other suitable attachment means.

In use, an activated device is formed by removing a first part 327 comprising a first reactive region 322 and a second part 329 comprising a second reaction region 324 from the tapes 321 and 323 through the perforations 326 and 328, respectively. The first part 327 and the second part 329 are then combined with the first reactive region 322 and the second reactive region 324 eclipsed and in contact, as explained in detail above.

Figure 3C:
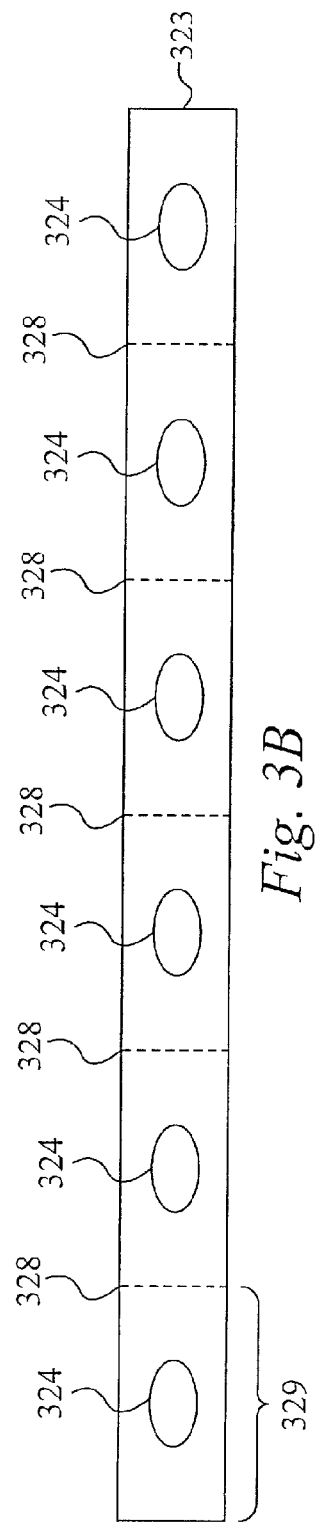
Figure 3C:
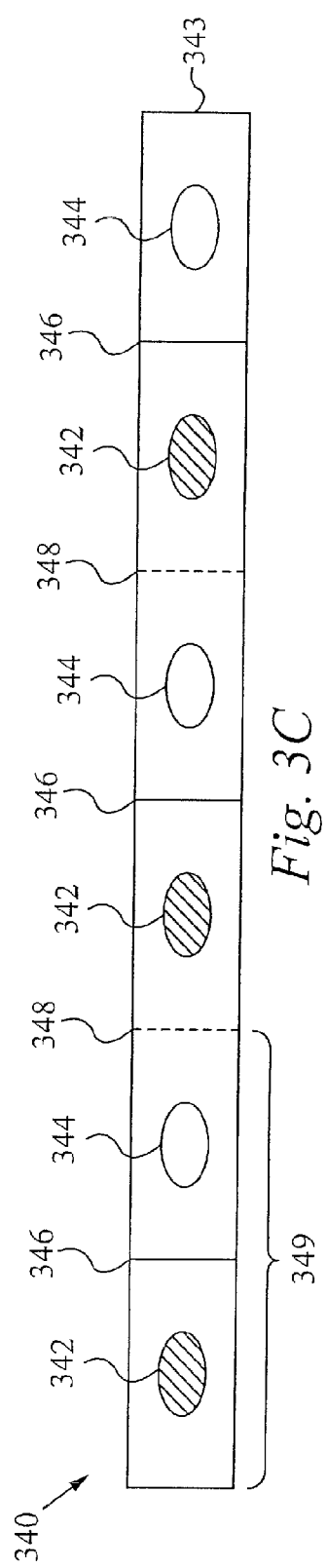

Now referring to FIG. 3C, in accordance with alternative embodiments of the invention, a system 340 comprises a plurality of first reactive regions 342 and second reactive regions 344 formed in an alternating fashion on single piece of tape 343. In use, an activated device is formed from a section 349 comprising a first reactive region 342 and a second reactive region 344 that is separated from the tape 343 through a perforation 348. The section 349 is then folded over onto itself through a seam 346, such that the first reactive region 342 and the second reactive region 348 are eclipsed and in contact with each other. While FIG. 3C, shows the first reactive regions 342 and the second reactive regions 344 being formed in an alternating fashion on single piece of tape 343 such that an active device is formed by folding one of the first reactive regions 342 and one of the second reactive regions 344 in an end-to-end fashion, it will be clear to one skilled in the art that a system can alternatively be formed on single piece of tape with first reactive regions and second reactive regions formed in rows, such that an active device is formed by folding one of the first reactive regions 342 and one of the second reactive regions 344 in a side-to-side fashion. It will be appreciated that forming first and second reactive regions using other configurations is also possible in accordance with the present invention.

Figure 4A:
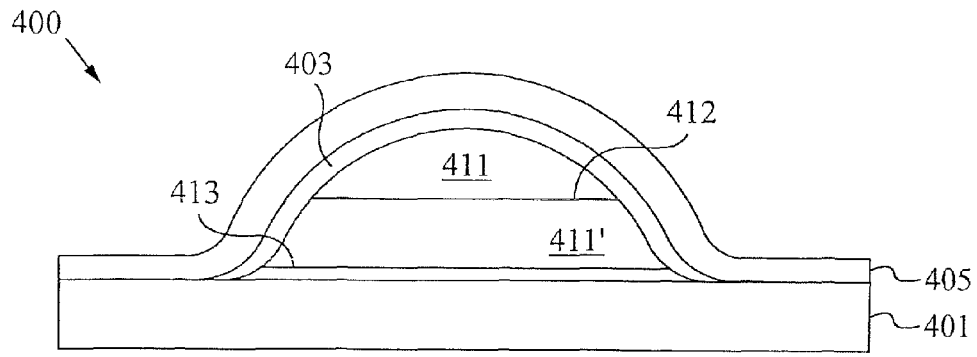

FIG. 4A shows a cross sectional view of a timing device 400, in accordance with the embodiments of the invention. As described previously, the device 400 comprises a lens 405 and a base 401. The device 400 also comprises an optical medium with one or more fluid layers 411 and 411' and a membrane structure 412 therebetween. The device 400 further comprises a lens coating layer 403 and a reactive material 413 that is capable of reacting with the lens coating layer 403. To activate the timing device 400, the membrane structure 403 is ruptured allowing the reactive material 413 to mix with the fluid layers 411 and 411' and react with the lens coating layer 403, thereby indicating the passage of a duration of time.

Figure 4B:
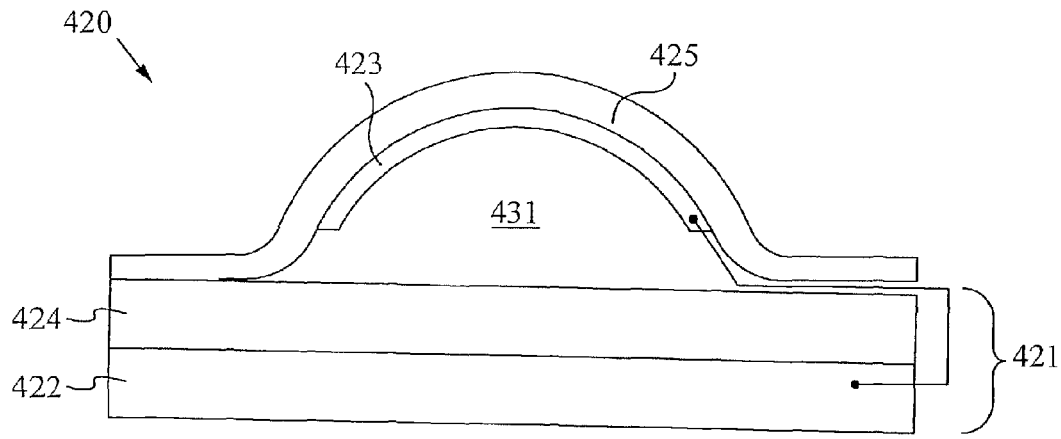

Referring now to FIG. 4B, a timing device 420, in accordance with further embodiments of the invention, comprises a lens 425, a metal base structure 421 and an ionic fluid medium or electrolyte 431, therebetween. The metal base structure 421 is formed from a first metal layer 424 with a first reduction potential and a second metal layer 422 with a second reduction potential that is substantially different from the first metal layer 424. The device 420 also has metal lens coating layer 423 with a reduction potential that is also substantially different from the first metal layer 424, but can be the same or nearly the same as the reduction potential of the second metal layer 422. To actuate the device the metal lens coating layer 423 and the second metal layer 422 are placed in electrical communication with each other. The potential difference between the first metal layer 424 and the second metal layer 422 will drive a current to flow and cause the metal lens coating layer 423 to become depleted over time, and plate out over the first metal layer, thereby indicating the passage of a duration of time.

In accordance with the embodiments of the invention, a timing device 420 comprises a lens 425 formed from a transparent polymer, such as polyester, or from a conductive polymer that is coated with a metal lens coating layer 423, such as aluminum. The timing device 420 further comprises a base structure 421 and a second electrode material 422. The second electrode material 422 can be any metal with a reduction potential that is different from a reduction potential of the first electrode material 423. Alternatively, the second electrode material 422 can be any metal with a reduction potential that is the same as the reduction potential of the first electrode material 423, when the device 420 is being operated as an electrolytic cell (viz. has a battery structure 421 or other source of electrons to drive the reduction and oxidation process). Between the first electrode material 423 and the base structure 421 is a colored electrolyte 431. When the timing device 420 is activated, the first electrode material 423 is depleted from the transparent lens 423 and the colored electrolyte 431 becomes visible, thereby indicating the passage of the duration of time.

In yet further embodiments of the invention, a metal screen (not shown) is in contact with one or both of the metal lens coating layer 423 and the second electrode material 422, to help ensure uniform depletion and/or plating of the electrode materials.

In still further embodiments of the invention, a timing device 420 comprises an electrolyte 431 with an indicator that changes when the device 420 is activated, such as described above, and the electrochemical cell generates a sufficient concentration of an ion or a pH altering species within the electrolyte.

Figure 4C:
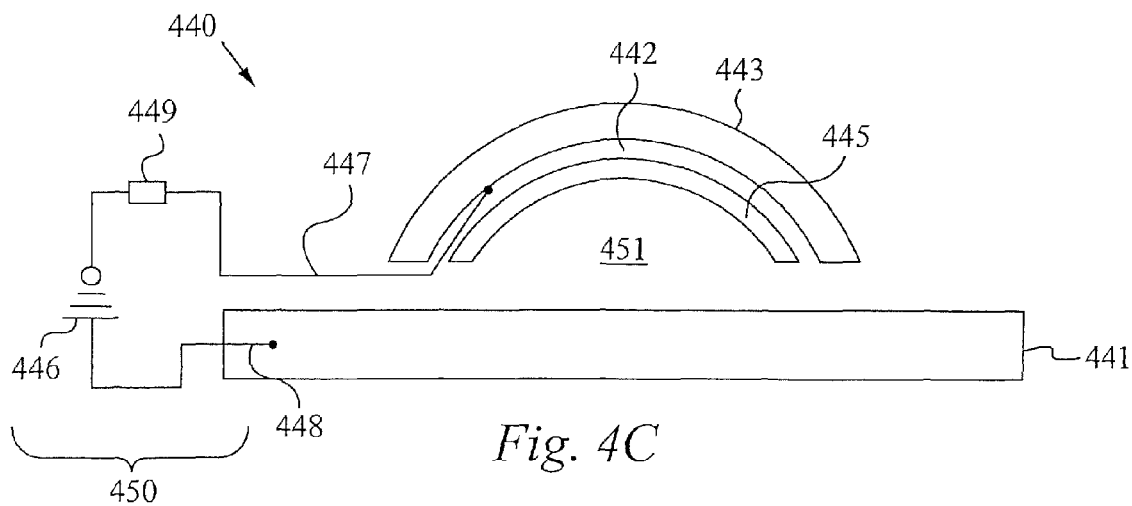

In accordance with yet further embodiments of the invention, a timing device 440 is coupled to a circuit 450, as shown in FIG. 4C. The device 440 comprises a lens 443, a metal base 441, a reactive medium 451 and a lens coating layer 445. The ionic reactive medium 451 is capable of depleting or dissolving the lens coating layer 445, either chemically or electrochemically as explained previously, when the device 440 is activated. After the device is activated and the lens coating layer 445 is sufficiently depleted or dissolved, the ionic reactive medium 451 provides an electrical path to close the circuit 450 between the leads 447 and 448. The circuit 450, in accordance with the embodiments of the invention, comprises a battery 446 and a piezo-electric element 449 that generate an audible signal when the device 440 expires and the circuit 450 is closed.

In still further embodiments of the invention, a timing device comprises a galvanic cell or an electrolytic cell, wherein one or more electrochemically active materials between a transparent lens and a base, such as metal ions and/or electrodes, are configured to be plated out or depleted and alters the visibility of the base through the lens and indicating the passage of a duration of time. Where a timing device is an electrochemical-based timing device, an actuator switch mechanism comprising electrical contacts can be used to actuate the device. The timing device, in accordance with still further embodiments of the invention, is in electrical communication with a thermosensor (not shown), wherein the thermosensor instructs the actuator switch to close a circuit between electrode elements of a galvanic or electrolytic cell within a range of temperatures.

Figure 5:
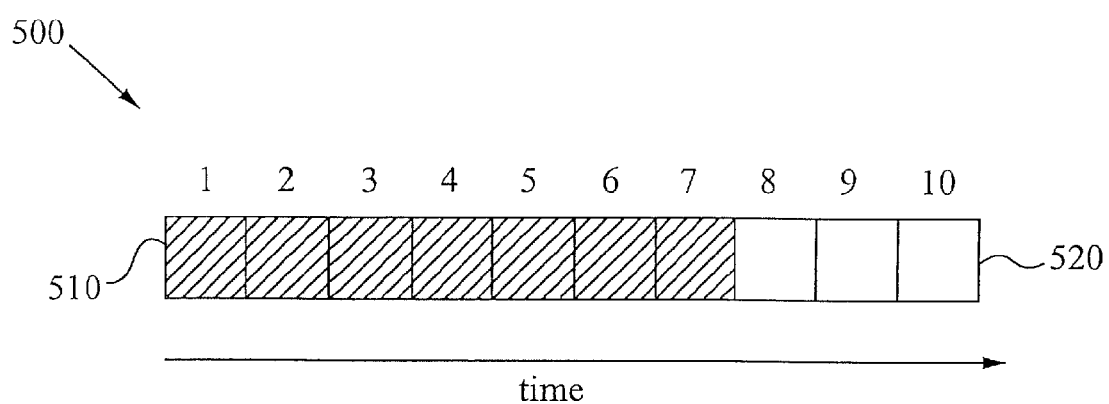
FIG. 5 shows a piece of timing film with a plurality of zones for indicating the passage of a range of times, in accordance with the embodiments of the invention.

Referring to FIG. 5, in accordance with yet further embodiments of the invention, a device comprises a film 500 with a plurality of zones (shown as 1-10). The zones can be arranged in any geometric pattern, but in some embodiments, are arranged in a linear fashion from a first end 510 to a second end 520 of the film 500. The zones are configured to change color at different rates and, therefore, provide an indication of the passage of a range of times. For example, when each of the zones represents one hour, then the film 500 as shown, indicates the passage of approximately 7 hours. In approximately one more hour, the next zone will change color and indicate the passage of approximately 8 hours.

Still referring to FIG. 5, each of the zones, in accordance with the embodiments of the invention, comprises a photographic, chemical and/or electro-chemical material, as described in detail above. When the zones (shown as 1-10) comprise photographic materials, the zones can be made to have different rates of reaction by using photographic materials with different sensitivities to heat, light and/or developer and/or by varying the thickness of diffusion layers deposited over each of the zones, such as described below. In accordance with an embodiment of the invention, the zones are made to have different rates of reaction and/or sensitivity to a developer by pre-treating the zones to a range of different light and/or heat exposures, wherein the zones with longer exposures will develop and change color faster than zones with shorter exposures after being activated.

Still referring to FIG. 5, when the zones (shown as 1-10) comprise chemical and/or electro-chemical material(s), as described in detail above and in accordance with the embodiments of the invention, the zones are made to have different rates of reactivity and/or sensitivity. Accordingly, each zone has a different expiration time and indicated passage of a different amount of time and the zones viewed collectively indicate passage of a total time. This embodiment has particular applications for managing inventories of food items in a household refrigerator by indicating how long the food items have been in the refrigerator, regardless of whether or not the food items have spoiled or aged past a freshness date.

Figure 6:
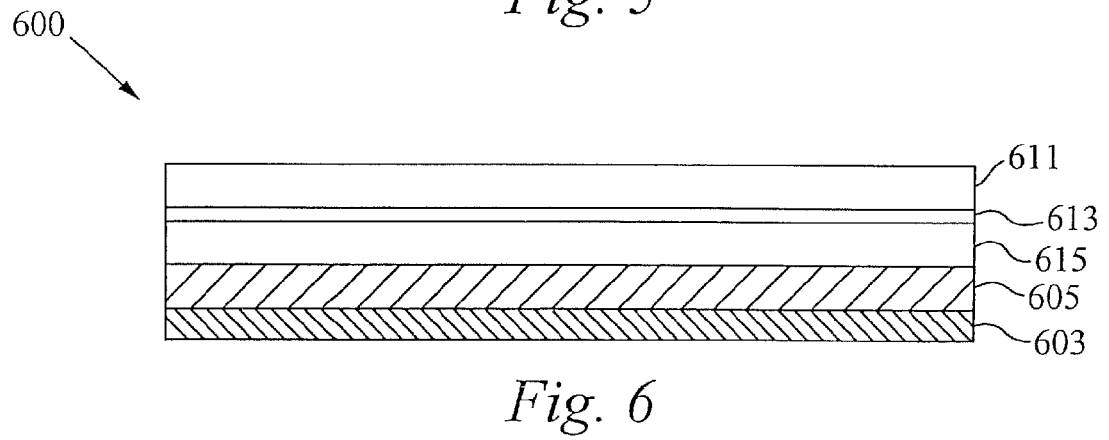
FIG. 6 is a cross-sectional representation of a section of timing film, in accordance with the embodiments of the invention.

FIG. 6 is a cross-sectional representation of a section of timing film 600, in accordance with the embodiments of the invention. The section of timing film 600 is formed by coating or depositing a photographic layer 605, which can include silver, silver halide, gelatin, cellulose, fatty acids, developers or combinations thereof, onto a base structure 603. In some embodiments, the base structure 603 is formed from a polymeric material, such as polyester, and can also include an adhesive layer (not shown) for attaching the section of timing film 600 to a consumer article (also not shown).

Still referring to FIG. 6, the section of film 600, in accordance with the embodiments of the invention, further comprises a diffusion layer 615 comprising a diffusion material and a developer layer 611 comprising a developer. The diffusion material is any material that will allow the developer in the developer layer 611 to migrate to the photographic layer 605 causing the photographic layer 605 to change color or darken and indicate the passage of time. Suitable diffusion materials include, but are not limited to, gelatin, cellulose and combinations thereof.

In accordance with still further embodiments of the invention, the section of film 600 further comprises a barrier layer 613 that can be pulled out or removed to activate the device and allow the developer layer 611 to diffuse through the layer 615 and cause the photographic layer 605 to change color or darken and indicate the passage of time. Alternatively, the photographic layer 605 and the developer layer 611 are formed as separate parts that can be brought together to activate the device, as explained in detail above with reference to FIGS. 3A-C.

FIG. 7A shows a cross-sectional view of a reactive region 700 of a timing device. The reactive region 700 of the timing device reacts to produce a visual change and indicate a passage of time, as explained above. The timing device can also include a lens and a base (not shown), such as described with reference to FIGS. 1A-B and FIG. 2.

Still referring to FIG. 7A, in accordance with the embodiments of the invention, the reactive region 700 comprises a first reactive portion 701 and a second reactive portion 703. The first reactive portion 701 and the second reaction portion 703 are, for example, metals with different reduction potentials that are capable of participating in the generation of an electrical potential in a galvanic cell or an electrolytic cell, as described previously. The reaction region 700 can also include an electrolyte 705 and electrical connections 711 and 713 which allow current to flow between the first reactive portion 701 and the second reaction portion 703 and generate a visual change to indicate a passage of time, as described above. In accordance with the embodiments of the invention, the reactive region 700 further comprises a compensating element 707 which is electrically coupled to the first reactive portion 701 and the second reactive portion 703 to compensate for changes in electrical potential and rates of reactions that can, and generally do, occur as a result of changes in temperature. The compensating element 707 can increase or decrease the rate that electrons flow through the electrical connections 711 and 713 with a change in temperature and the response to changes in temperature will depend on the application at hand. Suitable compensating elements include, but are not limited to, varistors, thermistors (both positive temperature compensating and negative temperature compensating thermistors) and/or combinations thereof. A varistor refers to an element that drops in resistance as the applied voltage across the varistor is increased. A positive temperature compensating thermistor refers to an element that drops in resistance as the temperature of the thermistor increases. A negative temperature compensating thermistor refers to an element that increases in resistance as the temperature of the thermistor increases.

Now referring to FIG. 7B, a timing device 720, in accordance the embodiments of the invention, comprises a lens 725, a metal base structure 721 and an ionic fluid medium or electrolyte 731, therebetween. The metal base structure 721 is formed from a first metal layer 724 with a first reduction potential and a second metal layer 722 with a second reduction potential that is substantially different from that of the first metal layer 724. The device 720 also has metal lens coating layer 723 with a reduction potential that is also substantially different from that of the first metal layer 724, but can be the same or nearly the same as the reduction potential of the second metal layer 722. To actuate the timing device 720 the metal lens coating layer 723 and the second metal layer 722 are placed in electrical communication with each other through connectors 731 and 733. The potential difference between the first metal layer 724 and the second metal layer 722 will drive a current to flow and cause the metal lens coating layer 723 to become depleted over time, and plate out over the first metal layer 724, thereby indicating the passage of a duration of time. Between the electrical connections 731 and 733 there is a compensating element 707, such as described above, that changes resistance in response to changes in applied potential, current flow, temperature or a combination thereof, thus making the timing device either more stable to the changes in temperature or more sensitive to the changes in temperature.

In accordance with yet further embodiments of the invention, a timing device utilizes an electrochromic material. An electrochromic material refers to a material that changes color when the composition of the material is changed by use of an electrochemical cell or other voltage source. Electrochromic materials often exhibit reversible color changes and can be switched between two or more color states by reversing the polarity of an applied potential of a layer comprising the material that is in contact with an ion or metal ion source, as described in detail below. A number of materials exhibit electrochromism, including but not limited to, tungsten oxide, molybdenum oxide, titanium oxide, niobium oxide, iridium oxide and rhodium oxide, to name a few.

FIG. 8A shows an exemplary reaction for electrochromic tungsten oxide 803, which is transparent. To change the color of the tungsten oxide 803, electrons 804 are provided from a cathodic site of the device which reduces ions or metal ions (M+) from an ion source 802. The reduced ions or atoms then combine with the tungsten oxide 803 to form a metal-tungsten oxide complex or structure 805 which is blue. The process can be reversed by oxidizing the metal-tungsten oxide complex or structure 805 at an anodic site of the device.

FIG. 8B shows a schematic representation of a multi-layered electrochromic device 800 in accordance with the embodiments of the invention. The electrochromic device 800 comprises containment layers 821 and 833, at least one of which is transparent so that color changes in an electrochromic layer 825 can be observed. The device 800 also has electrode layers 823 and 829, an electrochromic layer 825 and a metal ion source layer 827 therebetween. The electrochromic layer 825 comprises one or more electrochromic materials and the metal ion source layer 827 comprises metal ions 822, such as those described above with respect to FIG. 8A. In operation, an electrical potential is applied across the electrode layers 823 and 829 and electrons 824 and 826 flow into the electrochromic layer 825 from the electrode layer 829. Metal ions 822 migrate from the metal ion source layer 827 into the electrochromic layer 825 where the metal ions are reduced by the electrons 824 and combine with an electrochromic material to produce a color change within the electrochromic layer 825. The electrical potential can be applied across the electrode layers 823 and 829 using a battery 832 that is electrically coupled to the electrode layer 823 and 829 through electrical connections 828 and 830 and one or more conductive layers 831. As described previously, the process can be reversed by reversing the polarity of the battery 832.

Now referring to FIG. 9A, a timing device 900, in accordance with the embodiments of the present invention, comprises a layered electrochromic structure 916, which can include transparent constrainment layers 901 and 907 with an electrochromic layer 905 therebetween, similar to that described with reference to FIG. 8B. The timing device 900 can also include a base structure 903 that is viewable through the layered electrochromic structure 916 when the electrochromic layer 905 is in a transparent color state. In some embodiments, the device 900 also includes a driver circuit 910 that includes a voltage source 926 (FIG. 9B) that is electrically coupled to the electrochromic layer 905 through electrical connections 911 and 913. When an electrical potential is applied across the electrochromic layer 905, the electrochromic structure 916 switches from transparent and opaque and/or colored or switches for opaque and/or colored to transparent depending on the polarity of the electrical potential that is applied.

Now referring to FIG. 9B, the driver circuit 910, in accordance with the embodiments of the invention, comprises a timing circuit 920, such as a digital timing circuit and a battery structure 926 for providing the electrical potential. The battery structure 926 comprises any suitable elements capable of generating an electrical potential sufficient to change the color state of the electrochromic layer 905 (FIG. 9A). Suitable battery elements include, but are not limited to, a first electrode structure 921, a second electrode structure 923 and an electrolyte structure 922. In operation, the timing circuit 920 can act as a switch that maintains an open circuit between the battery structure 926 and the electrochromic layer 905 (FIG. 9A) for a prescribed period of time and then closes the circuit between the battery structure 926 and the electrochromic layer 905 after the prescribed period of time causing a color change in the layered electrochromic structure 916 (FIG. 9A).

In accordance with yet further embodiments the invention, the driver circuit 910 is programmable and can be programmed to switch or change the color state of the layered electrochromic structure 916 in a range of prescribed times that are selectable by the user and/or manufacturer. In still further embodiments of the invention, the layered electrochromic structure 916 is divided into zones, wherein the zones are activated in a range of prescribed times and the zones individually or collectively change color to indicate the passage of time or the passage of a range of times, such as previously described with reference to FIG. 5.

In accordance with still further embodiments of the invention, a timing device comprises an electrochemical cell configuration, such as described with respect to FIGS. 4B-C and 7B, wherein the timing device comprises a plurality of sub cells or zones that individually or collectively indicate the passage of time or the passage of a range of times, such as previously described with reference to FIG. 5. For example, a timing device is configured with a plurality of sub cells or zones that each includes a first set of electrodes formed from a first electrode material. The first electrodes are electrically isolated from each other and are in electrical communication with a second electrode or second set of electrodes formed from a second electrode material through resistors having a range of different resistivities.

Now referring to FIG. 10 showing a schematic representation of a timing device 250 with an electrochemical structure 252 and an indicating layer 257. The electrochemical structure 252 can be configured in any number of different ways, such as described above, but in some embodiments, comprises an indicating electrolyte 253, a top electrode 255 and a bottom electrode 251. In operation, the device 250 is activated through an activating mechanism (not shown) and the top electrode 255 is depleted or partially depleted. The indicating electrolyte 253 then contacts the indicating layer 257 and changes the appearance of the indicating layer 257. For example, the indicating electrolyte 253 is colored and the indicating layer 257 is formed from a porous or an absorbent material, such as cellulose. When the top electrode 257 is depleted, or partially depleted, the indicating electrolyte 253 is absorbed into the indicating layer 257 providing a visual indication of a passage of time. The timing device 250 can also include a protective cover 258 or clear lens, such as described previously. The indicating layer 257 helps to provide a uniform visual indication of the passage of time, even when depletion, or partial depletion, of the top electrode 255 is not uniform. The timing device 250 can also be equipped with a compensating element (not shown) and any other number of auxiliary elements, such as described with reference to the previous embodiments. Further, it is understood that the timing device 250 can be sectionalized or compartmentalized to indicate the passage of a range of times, also described with reference to previous embodiments.

Referring now to FIG. 11 showing a schematic representation of timing device 105 comprising a solid-state electrolyte 151 that is sandwiched between electrode structures 153 and 155. The electrode structures 153 and 155 can be formed from any number of different materials and combinations of materials, including metal coated polymer. For example, the solid-state electrolyte 151 comprises one or more materials selected from the group of silver halide (e.g. AgI and RbAg$_4$I$_5$), silver selenide (e.g. Ag$_2$Se), sodium ion complexes (e.g. sodium β-Aluminum and NASICON), lithium ion complexes (e.g. LiCoO$_2$, LiNiO$_2$ and LiMnO$_2$), oxides (e.g. cubic stabilized ZrO$_2$, δ-Bi$_2$O$_3$, and defect Perovskites) and Fluoride ion complexes (e.g. PbF$_2$, BaF$_2$, SrF$_2$ and CaF$_2$). In operation, the electrode structures 153 and 155 are electrically coupled through an activating mechanism 157 that is a switch, a timing circuit or any other activating mechanism. Electrically coupling the electrode structures 153 and 155 results in the depletion or partial depletion of one or more electrode materials and provides an indication of the passage of time. The timing device 150 with the solid-state electrolyte 151 can, in accordance with the embodiments of the invention, be formed as a plurality of sub cells or zones that individually or collectively indicate the passage of time or the passage of a range of times, such as previously described with reference to FIG. 5.

Referring now to FIG. 12, a solid-state timing device 350 is formed in parts with a first electrode structure 352 formed on a first piece of a substrate 351 and a second electrode structure 354 formed on a second piece of the substrate 351'. The first electrode structure 352 comprises a first metal layer 359 and a solid-state electrolyte layer 361 formed thereon. The second electrode structure 354 comprises a second metal layer 355, wherein the first metal layer 359 and the second metal layer 355 are formed from metals with different reduction potentials, such as described in detail above.

Still referring to FIG. 12, the first piece of the substrate 351 and the second piece of the substrate 351' can be formed from any number of different materials or combinations of materials, such as glass, metal or plastic. In some embodiments, the first piece of the substrate 351 and the second piece of the substrate 351' are formed from plastic, such as polyester or another similar transparent material. In accordance with further embodiments of the invention, removable protective layers 353 and 357 are formed over the first electrode structure 352 and the second electrode structure 354, respectively. In operation, the protective layers 353 and 357 are removed and the first piece of the substrate 351 and the second piece of the substrate 351' are folded along a fold or perforation 363 as indicated by the arrow 365, such that the first electrode structure 352 and the second electrode structure 354 make ohmic contact and actuate the timing device 350. As described in detail above, depletion of at least one of the metal layers 359 and 355 provides a visual indication of a passage of a duration of time through one of the first piece of the substrate 351 and the second piece of the substrate 351'.

In accordance with still further embodiments of the invention, the timing device 350 comprises a switch mechanism (not shown), a compensating element (not shown) and/or an indicator layer (not shown), such as described above. Further, one or both of the first and second electrode structures 352 and 354 can be divided into sub-cells or zones, such that the sub-cells or zones collectively provide a visual indication of a passage of a range of durations of time.

Referring now to FIGS. 13A-B, a timing device 1300 includes, in accordance with the embodiments of the invention, an electrode structure 1304 that has a grid array architecture. The timing device 1300 includes an electrolyte layer 1315 that is formed or placed on a suitable base layer 1321. The base layer 1321 is formed from any suitable material including, but not limited to, plastic, glass, metal and combinations thereof. On top of or over the electrolyte layer 1315 is the electrode structure 1304. The electrode structure 1304 includes an anode layer 1301 and a cathode layer 1302. In some embodiments, the cathode layer 1302 does not contact the electrolyte layer 1315 and is separated from the electrolyte layer 1315 by an insulating layer 1319. The anode layer 1301 is in contact with the electrolyte layer 1315. The electrolyte layer 1315 is formed from a solid-sate material, a liquid material, a gel material and/or a semi-solid paste material.

Still referring to FIGS. 13A-B, a thermistor layer 1305 is preferably formed along side of the anode layer 1301 and the cathode layer 1302. Also, an array of cathode line structures 1313 and 1313' are formed over the anode layer 1301 and the thermistor layer 1305 to provide electrical contacts between the thermistor layer 1305 and the anode layer 1301. There is also at least one contact line 1317 between the cathode layer 1302 and the thermistor layer 1305. The anode layer 1301, the cathode layer 1302, the thermistor layer 1305, the cathode line structures 1313 and 1313' and the contact line 1317 can be formed using any suitable technique known in the art including, but not limited to, vapor deposition, sputtering and micro-printing techniques.

The timing device 1300 with a grid array architecture preferably includes a mechanism for activating the timing device, such as described above. When the timing device 1300 is activated, the anode layer 1301 begins to deplete in a direction away from the cathode layer 1302, as indicated by the arrow 1311, thereby exposing sequentially positioned cathode line structures 1313 and 1313'. The exposed cathode line structures provide points of internal resistance to current flow and thus control the rate that the anode layer 1301 is depleted. The number, the spacing, the thicknesses and geometries of the cathode line structures 1313 and 1313' as well as the anode layer 1301, the cathode layer 1302 and the thermistor layer 1305, are designed or tailored for the application at hand. Further, the material used to form the thermistor layer 1305, in accordance with the embodiments of the invention, is selected to regulate the overall depletion rate of the anode layer 1301 to be temperature independent. As described in detail above, a timing device, such as the timing device 1300, includes a protective lens or window 1323 through which depletion of the anode layer 1301 is directly or indirectly is observed.

The current invention has applications for marking when any number of different events need to take place and/or for timing the duration of any number of different events. For example, the timing device of the present invention has applications for indicating when perishable materials have expired and need to be thrown out, indicating the age of inventory and managing when the inventory needs to be rotated, tracking a deadline and a host of other time and/or temperature dependent events. One advantage of the present invention is that the timing device can be fabricated in two or more reactive parts, wherein the device is not activated, or made sensitive to the environment (such as temperature), until the parts are electrically coupled together, as explained in detail above. Accordingly, the shelf life of the timing device prior to use is enhanced and the sensitivity of the device to environmental conditions prior to use is reduced.

The present invention has been described in terms of specific embodiments incorporating details to facilitate the understanding of the principles of construction and operation of the invention. As such, references, herein, to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A timing device comprising an electrochemical structure, the electrochemical structure comprising an electrolyte and electrodes in electrical communication with the electrolyte, wherein depletion of one or more of the electrodes provides an indication of a passage of a duration of time, further wherein the electrochemical structure is divided into isolated zones configured to change color at different rates to collectively provide a visual indication of the passage of the duration of time.

2. The timing device of claim 1, further comprising means to initiate depletion of the one or more electrodes.

3. The timing device of claim 1, wherein the electrolyte comprises a material selected from the group consisting of a silver halide, a silver selenide, a sodium ion complex, a lithium ion complex, an oxide and a Fluoride ion complex.

4. A timing device comprising:
 a. electrode structures;
 b. an electrolyte sandwiched between the electrode structures; and
 c. an actuator to actuate depletion of a portion of at least one of the electrode structures and thereby indicate a passage of a duration time, wherein the at least one of the electrode structures comprises a plurality of corresponding sub cells, each of the sub cells isolated from each other, and having different resistivities.

5. A timing device comprising an electrochemical structure, the electrochemical structure comprising an electrolyte and electrodes in electrical communication with the electrolyte, wherein depletion of one or more of the electrodes provides an indication of a passage of a duration of time, further wherein the electrochemical structure is divided into zones that collectively provide a visual indication of the passage of the duration of time, wherein each of the zones comprise different materials.

6. The timing device of claim 5, further comprising means to initiate depletion of the one or more electrodes.

7. The timing device of claim 5, wherein the electrolyte comprises a material selected from the group consisting of a silver halide, a silver selenide, a sodium ion complex, a lithium ion complex, an oxide and a Fluoride ion complex.

8. A timing device comprising:
 a. electrode structures;
 b. an electrolyte sandwiched between the electrode structures; and
 c. an actuator to actuate depletion of a portion of at least one of the electrode structures and thereby indicate a passage of a duration time, wherein the at least one of the electrode structures comprises a plurality of corresponding sub cells, each of the sub cells comprising different materials.

9. A timing device comprising:
 a. electrode structures;
 b. an electrolyte sandwiched between the electrode structures; and
 c. an actuator to actuate depletion of a portion of at least one of the electrode structures and thereby indicate a passage of a duration time, wherein the at least one of the electrode structures comprises a plurality of corresponding sub cells, each of the sub cells having separate resistivities.

* * * * *